United States Patent [19]
Andrews et al.

[11] Patent Number: 5,919,819
[45] Date of Patent: Jul. 6, 1999

[54] DIHYDROPYRAN DERIVATIVES AS VIRAL NEURAMINIDASE INHIBITORS

[75] Inventors: David Andrews, Shefford; Paul Jones, Harpenden; David Humber, Surrey, all of United Kingdom

[73] Assignee: Biota Scientific Management Pty Ltd., Melbourne, Australia

[21] Appl. No.: 09/000,149

[22] PCT Filed: Aug. 7, 1996

[86] PCT No.: PCT/AU96/00495

§ 371 Date: Sep. 14, 1998

§ 102(e) Date: Sep. 14, 1998

[87] PCT Pub. No.: WO97/06157

PCT Pub. Date: Feb. 20, 1997

[30] Foreign Application Priority Data

Aug. 8, 1995 [GB] United Kingdom ............... 9516276

[51] Int. Cl.⁶ .................. A61K 31/35; C07D 315/00
[52] U.S. Cl. ......................... 514/459; 549/424
[58] Field of Search ................. 549/424; 514/459

[56] References Cited

FOREIGN PATENT DOCUMENTS

| 27242/92 | 4/1993 | Australia . |
| 92/06691 | 4/1992 | WIPO . |
| 95/18800 | 7/1995 | WIPO . |

*Primary Examiner*—Deborah C. Lambkin
*Attorney, Agent, or Firm*—Foley & Lardner

[57] ABSTRACT

Compounds of formula (I), wherein $R^1$ represents $NR^5R^6$, wherein $R^5$ represents H or a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group; and $R^6$ represents a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group; $R^2$ represents a group $SO_2R^9$ or $COR^9$; $R^3$ represents H, $C_{1-6}$-alkyl or $C(=NR^{11})NR^{12}R^{13}$; $R^4$ represents H or $C_{1-6}$alkyl; $R^7$ and $R^8$ each independently represent H, $C_{1-6}$alkyl or $COR^9$; $R^9$ represents $C_{1-6}$alkyl optionally substituted by one or more halogen atoms; $R^{10}$ represents H, $C_{1-6}$-alkyl or phenyl; $R^{11}$, $R^{12}$ and $R^{13}$ each independently represent H, $C_{1-6}$alkyl, amino, hydroxy, cyano or nitro; and X represents O or S; and their pharmaceutically acceptable derivatives are neuraminidase inhibitors useful in the treatment of viral infections.

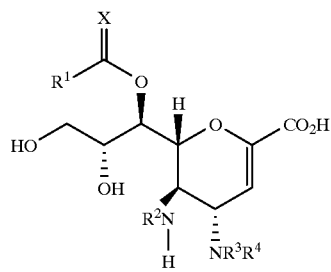

(I)

16 Claims, No Drawings

DIHYDROPYRAN DERIVATIVES AS VIRAL NEURAMINIDASE INHIBITORS

This invention relates to a new class of chemical compounds and to their use in medicine. In particular the invention concerns novel dihydropyran derivatives, methods for their preparation, pharmaceutical formulations thereof and their use as antiviral agents.

Enzymes with the ability to cleave N-acetyl neuraminic acid (NANA), also known as sialic acid, from other sugars are present in many microorganisms. These include bacteria such as Vibrio cholerae, Clostridium perfringens, Streptococcus pneumoniae, and Arthrobacter sialophilus, and viruses such as influenza virus, parainfluenza virus, mumps virus, Newcastle disease virus, and Sendai virus. Most of these viruses are of the orthomyxovirus or paramyxovirus groups, and carry a neuraminidase activity on the surface of the virus particles.

Many of the neuraminidase-possessing organisms are major pathogens of man and/or animals, and some, such as influenza virus and Newcastle disease virus, cause diseases of enormous economic importance. It has long been thought that inhibitors of neuraminidase activity might prevent infection by neuraminidase-bearing viruses. Most of the known neuraminidase inhibitors are analogues of neuraminic acid, such as 2-deoxy-2,3-didehydro-N-acetylneuraminic acid (DANA) and its derivatives. See, e.g., Meindl et al., Virology 1974 58 457–63. International Application Publication No. WO91/16320 describes a number of analogues of DANA active both in vitro and in vivo against viral neuraminidase and useful in the treatment of influenza. A number of substituted guanidino derivatives were described in EP 539204. International Application Publication No: WO95/18800 describes the methanesulphonamide analogue of DANA and the trifluoroacetate analogue of DANA is described in International Application Publication No. WO95/20583.

We have now found a novel class of dihydropyran derivatives which are active against the influenza virus.

The invention therefore provides, in a first aspect, compounds of formula (I)

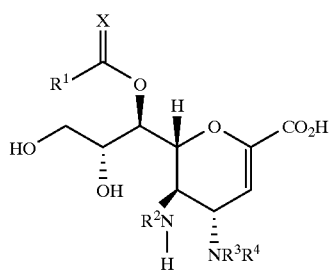

wherein
$R^1$ represents $NR^5R^6$, wherein
$R^5$ represents H or a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group; and
$R^6$ represents a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group;
$R^2$ represents a group $SO_2R^9$ or $COR^9$;
$R^3$ represents H, $C_{1-6}$alkyl or $C(=NR^{11})NR^{12}R^{13}$;
$R^4$ represents H or $C_{1-6}$alkyl;
$R^7$ and $R^8$ each independently represent H, $C_{1-6}$alkyl or $COR^9$;
$R^9$ represents $C_{1-6}$alkyl optionally substituted by one or more halogen atoms;
$R^{10}$ represents H, $C_{1-6}$alkyl or phenyl;
$R^{11}$, $R^{12}$ and $R^{13}$ each independently represent H, $C_{1-6}$alkyl, amino, hydroxy, cyano or nitro;
X represents O or S; and their pharmaceutically acceptable derivatives.

In general, it is to be understood that when any variable occurs more than once in formula (I), that variable may be the same on each occasion, or different. In particular, when $R^5$ and $R^6$ each represent an optionally substituted hydrocarbon group or a heteroaromatic group they may be the same or different.

As used herein, "hydrocarbon group" includes saturated and unsaturated, straight, branched and cyclic hydrocarbon groups, including aryl groups, and combinations of such groups.

Suitable hydrocarbon groups represented by $R^6$ and/or $R^5$ include $C_{1-20}$alkyl, such as propyl, butyl, pentyl, hexyl, heptyl, octanyl, nonyl, decyl, undecyl and dodecyl, $C_{5-7}$cycloalkyl groups, such as cyclohexyl, phenyl and aralkyl groups such as benzyl. Suitable substituents for the hydrocarbon groups represented by $R^6$ and/or $R^5$ include Br, Cl, F, I, $CF_3$, $NH_2$, substituted amino groups such as $NHCO(C_4H_{10})$, alkoxy groups such as methoxy, and hydroxy.

When $R^5$ and/or $R^6$ represents a heteroaromatic group, this will suitably be a pyridyl group optionally substituted by one or more of $C_{1-6}$-alkyl, Br, Cl, F, I and $CF_3$.

Preferably R5 represents H, $C_{1-6}$-alkyl or benzyl.
Preferably $R^6$ represents optionally substituted $C_{1-20}$alkyl or benzyl.
More preferably $R^5$ represents H, $C_{1-3}$alkyl or benzyl and $R^6$ represents $C_{1-12}$alkyl optionally substituted by an unsubstituted or substituted amine, or benzyl.
Preferably $R^2$ represents $COR^9$.
Where $R^3$ represents $C(=NR^{11})NR^{12}R^{13}$, suitably two of $R^{11}$, $R^{12}$ and $R^{13}$ represent H and the other of $R^{11}$, $R^{12}$ and $R^{13}$ is selected from H, $C_{1-6}$alkyl, such as methyl, $NH_2$, OH, CN or $NO_2$.
Preferably $NR^3R^4$ represents amino or guanidino, more preferably guanidino.
Preferably $R^9$ represents methyl or trifluoromethyl, more preferably methyl. Preferably X represents O.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof at any of the functional groups in the compounds of formula (I). Of particular interest as such derivatives are compounds modified at the carboxyl function, hydroxyl functions or at amino groups. Thus compounds of interest include alkyl (such as methyl, ethyl or propyl e.g. isopropyl) or aryl (e.g. phenyl, benzoyl) esters and acetyl esters of the compounds of formula (I).

It will be appreciated by those skilled in the art that the pharmaceutically acceptable derivatives of the compounds of formula (I) may be derivatised at more than one position.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene- p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

A particular subgroup of compounds according to the invention is represented by formula (Ia):

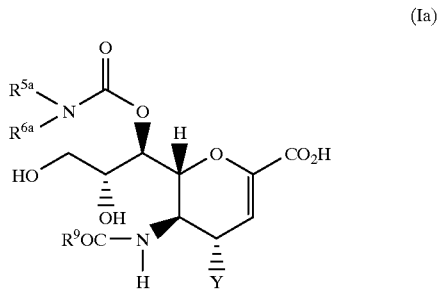

(Ia)

wherein:
$R^9$ is as defined for formula (I); $R^{5a}$ represents H, $C_{1-12}$alkyl or benzyl;
$R^{6a}$ represents optionally substituted $C_{1-12}$alkyl or benzyl;
Y represents an amino or guanidino group; and pharmaceutically acceptable salts or esters thereof.

When $R^{6a}$ represents optionally substituted $C_{1-12}$alkyl, suitable substituents include substituted and unsubstituted amines.

Particular compounds according to the invention include:
(4S,5R,6R)-5-Acetylamino6-(1R-heptylcarbamoyloxy-2R,3-dihydroxy-propyl)-4-guanidino-5,6-dihydro-4H-pyran-2-carboxylic acid;
(4S,5R,6R)-5-Acetylamino6-(1R-dodecylcarbamoyloxy-2R,3-dihydroxy-propyl)-4-guanidino-5,6-dihydro4H-pyran-2-carboxylic acid;
(4S,5R,6R)-5-Acetylamino-6-{1R-[(6-amino-hexyl) carbamoyloxy]-2R,3-dihydroxypropyl}4-guanidino-5, 6-dihydro4H-pyran-2-carboxylic acid; and pharmaceutically acceptable derivatives thereof.

References hereinafter to a compound of the invention include the compounds of formula (I) and pharmaceutically acceptable derivatives thereof.

The compounds of formula (I) possess antiviral activity. In particular these compounds are inhibitors of viral neuraminidase of orthomyxoviruses and paramyxoviruses in particular neuraminidase, for example the viral neuraminidase of influenza A and B, parainfluenza, mumps and Newcastle disease.

There is thus provided in a further aspect of the invention a compound of formula (I) or a pharmaceutically acceptable derivative thereof for use as an active therapeutic agent in particular as an antiviral agent for example in the treatment of orthomyxovirus and paramyxovirus infections.

In a further or alternative aspect there is provided a method for the treatment of a viral infection, for example orthomyxovirus and paramyxovirus infections in a mammal including man comprising administration of an effective amount of a compound of formula (I) or a pharmaceutically acceptable salt or derivative thereof.

In a preferred aspect there is provided a method for the treatment of influenza A or B in a mammal including man comprising administration of an effective amount of a compound of formula (I) or a pharmaceutically acceptable salt or derivative thereof.

There is also provided in a further or alternative aspect use of a compound of the invention for the manufacture of a medicament for the treatment of a viral infection.

It will be appreciated by those skilled in the art that reference herein to treatment extends to prophylaxis as well as the treatment of established infections or symptoms.

The compounds of the invention may also be used in diagnostic methods, in particular methods for the detection of influenza virus. For use in such methods it may be advantageous to link a compound of the invention to a label.

It will be further appreciated that the amount of a compound of the invention required for use in treatment will vary not only with the particular compound selected but also with the route of administration, the nature of the condition being treated and the age and condition of the patient and will ultimately be at the discretion of the attendant physician or veterinarian. In general however a suitable dose will be in the range of from about 0.1 to 750 mg/kg of bodyweight per day, preferably in the range of 0.5 to 60 mg/kg/day, most preferably in the range of 1 to 20 mg/kg/day.

Treatment is preferably commenced before or at the time of infection and continued until virus is no longer present in the respiratory tract. However the compounds are also effective when given post-infection, for example after the appearance of established symptoms.

Suitably treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form for example containing 10 to 1500 mg, conveniently 20 to 1000 mg, most conveniently 50 to 700 mg of active ingredient per unit dosage form.

While it is possible that, for use in therapy, a compound of the invention may be administered as the raw chemical it is preferable to present the active ingredient as a pharmaceutical formulation The invention thus further provides a pharmaceutical formulation comprising a compound of formula (1) or a pharmaceutically acceptable salt or derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration to the respiratory tract (including the nasal passages) for example by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For administration to the respiratory tract (including intranasal administration) according to the method of the invention the neuraminidase inhibitors may be administered by any of the methods and formulations employed in the art for administration to the respiratory tract.

Thus in general the compounds may be administered in the form of a solution or a suspension or as a dry powder.

Solutions and suspensions will generally be aqueous for example prepared from water alone (for example sterile or pyrogen-free water) or water and a physiologically acceptable co-solvent (for example ethanol, propylene glycol, polyethlene glycols such as PEG 400).

Such solutions or suspensions may additionally contain other excipients for example preservatives (such as benzalkonium chloride), solubilising agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant such as a chlorofluorocarbon (CFC) for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronisation.

When desired, formulations adapted to give sustained release of the active ingredient may be employed.

The compounds of the invention may also be used in combination with other therapeutic agents, for example other anti-infective agents. In particular the compounds of the invention may be employed with other antiviral agents. The invention thus provides in a further aspect a combination comprising a compound of formula (I) or a pharmaceutically acceptable salt or derivative thereof together with another therapeutically active agent, in particular an antiviral agent.

The combinations referred to above may conveniently be presented for use in the form of a pharmaceutical formulation and thus such formulations comprising a combination as defined above together with a pharmaceutically acceptable carrier therefor comprise a further aspect of the invention.

Suitable therapeutic agents for use in such combinations include other anti-infective agents, in particular antibacterial and anti-viral agents such as those used to treat respiratory infections. For example, other compounds effective against influenza viruses, such as amantadine, rimantadine and ribavirin, may be included in such combinations.

The individual components of such combinations may be administered either sequentially or simultaneously in separate or combined pharmaceutical formulations.

When the compounds of the invention are used with a second therapeutic agent active against the same virus the dose of each compound may either be the same as or differ from that employed when each compound is used alone. Appropriate doses will be readily appreciated by those skilled in the art.

The compounds of formula (I) and their pharmaceutically acceptable salts and derivatives may be prepared by the methods described below in which $R^1$, $R^2$, $R^3$, $R^4$ and X are as defined for formula (I) unless otherwise specified. The methods outlined below form a further aspect of the invention.

In one such process (A) compounds of formula (I) wherein $R^3$ and $R^4$ each represent H may be prepared from compounds of formula (II)

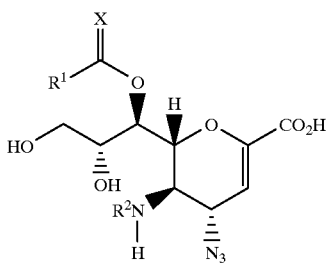

(II)

or a suitably protected derivative thereof, by reduction of the azide group, followed, if necessary, by deprotection.

The reduction may be carried out using any known methods for the conversion of azides to amines. Suitable methods are described in the Examples hereinafter and, for example, in International patent applications publication numbers 93/12105 and 95/00503.

According to a second process, (B), compounds of formula (I) may be prepared from intermediates of formula (III):

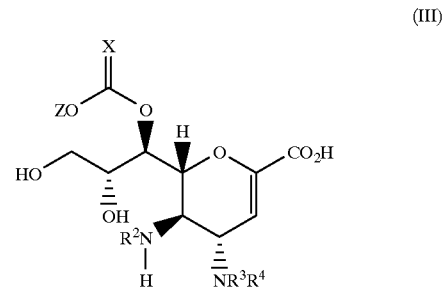

(III)

or protected derivatives thereof wherein Z represents an activating group, for example para-nitrophenyl, by reaction with a compound of formula $HNR^5R^6$ in the presence of a base, such as an organic base, for example, pyridine and, preferably, a suitable catalyst, such as dimethylaminopyridine (DMAP).

Compounds of formula (I) may also be prepared from other compounds of formula (I) by interconversion reactions. For example, compounds wherein $R^3$ and $R^4$ are other than H may be prepared by derivatisation of the corresponding compound wherein $R^3$ and/or $R^4$ are H. In particular, compounds of formula (I) wherein $R^3$ represents $C(=NR^{11})$ $NR^{12}R^{13}$ may be prepared from corresponding compounds of formula (III) wherein $R^3$ is H, for example, by reaction with pyrazolcarboxamidine, or a derivative thereof.

Similarly, compounds of formula (I) may be converted to their pharmaceutically acceptable derivatives, e.g. salts or esters, by conventional techniques.

Compounds of formula (II) may be prepared from the corresponding compounds of formula (IV):

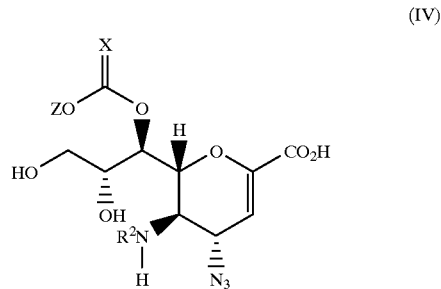

(IV)

or protected derivatives thereof, wherein Z is as previously defined, analogously to the preparation of compounds of formula (I) from compounds of formula (III). Intermediates of formula (III) and (IV) may be prepared from the corresponding compounds of formula (V):

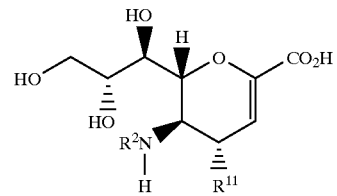

(V)

or protected derivatives thereof, wherein $R^{11}$ represents $NR^3R^4$ as previously defined or $N_3$, by reaction with a compound of formula ZOC(=X)CI in the presence of a base, such as an organic base, for example, pyridine and, preferably, a suitable catalyst such as, for example, DMAP.

Compounds of formula (V) are known compounds. Their preparation is described, for example, in International Patent Application publication No. 91/16320.

Intermediates of formulae (II), (III) and (IV) are novel compounds and comprise a further aspect of the present invention.

As will be appreciated by those skilled in the art it may be necessary or desirable at any stage in the above described processes to protect one or more sensitive groups in the molecule to prevent undesirable side reactions; the protecting group may be removed at any convenient subsequent stage in the reaction sequence.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene and P G M Wuts (John Wiley and Sons 1991).

Conventional amino protecting groups may include for example aralkyl groups, such as benzyl, diphenylmethyl or triphenylmethyl groups; and acyl groups such as N-benzyloxycarbonyl or t-butoxycarbonyl.

Hydroxy or carboxy groups may be protected, for example, by aralkyl groups, such as benzyl, diphenylmethyl or triphenylmethyl groups, acyl groups, such as acetyl, acetal, silicon protecting groups, such as trimethylsilyl groups, or as tetrahydropyran derivatives.

Removal of any protecting groups present may be achieved by conventional procedures.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

The present invention is further described by the following examples which are for illustrative purposes only and should not be construed as a limitation of the invention.

EXAMPLE 1

(4S,5R,6R)-5-Acetylamino4-amino6-(1R-heptylcarbamoyloxy-2R,3-dihydroxy-propyl)-5,6-dihydro4H-pyran-2-carboxylic acid trifluoroacetate Intermediate (1): (4S,5R, 6R)-5-Acetylamino-4-azido6-[(S)-hydroxy-(2-oxo-[1,3]dioxolan-4R-yl)-methyl]-5,6-dihydro4H-pyran-2-carboxylic acid methyl ester To a suspension of (4S,5R,6R)-5-Acetylamino4-azido6-(1R,2R,3-trihydroxy-propyl)-5,6-dihydro4H-pyran-2-carboxylic acid methyl ester (8.2 g) in dry acetonitrile (100 ml) and dry dichloromethane (200 ml) was added 4-dimethylaminopyridine (8.6 g). A 20% solution of phosgene in toluene (18 ml) was added slowly dropwise and the reaction mixture was stirred at room temperature for 2 hours. The solution was then added to ice cold 1M potassium dihydrogen orthophosphate solution (400 ml) and extracted with ethyl acetate (350 ml×3). The combined organic extracts were washed with saturated aqueous NaCl (30 ml), dried ($Na_2SO_4$), and the solvent removed under vacuum to yield an orange foam which was purified by flash chromatography on a silica column (Merck 9385, chloroform/methanol 15:1) to give the title compound (6.008 g) as an off-white foam.

TLC silica (chloroform/methanol 15:1) Rf 0.13
m/z $MNH_4^+$=374

Intermediate (2): (4S,5R,6R)-5-Acetylamino-4-azido-6-[(S)-heptylcarbamoyloxy-(2-oxo-[1,3]dioxolan4R-yl)-methyl]-5,6-dihydro-4H-pyran-2-carboxylic acid methyl ester To an ice-cold solution of Intermediate 1(1 g) in dry dichloromethane (10 ml) was added 4-dimethylaminopyridine (349 mg) and n-heptyl isocyanate (1 g). The solution was warmed to room temperature and stirred for 21 hours under nitrogen. The reaction was then quenched by the addition of methanol (1 ml) and the solution stirred for 15 min then added to ice cold 1M potassium dihydrogen orthophosphate solution (100 ml) and extracted with ethyl acetate (175 ml×3). The combined organic extracts were washed with concentrated aqueous NaCl (30 ml), dried ($Na_2SO_4$) and the solvent removed under vacuum to yield an orange solid which was purified by flash chromatography on a silica column (Merck 9385, chloroform/methanol 20:1) to give the title compound (560 mg) as a white foam.

TLC silica (chloroform/methanol 9:1) Rf 0.34
m/z $MH^+$=498

(4S,5R,6R)-5-Acetylamino4-amino6-(1R-heptylcarbamoyloxy-2R,3-dihydroxy-propyl)-5,6-dihydro-4H-pyran-2-carboxylic acid trifluoroacetate A mixture of Intermediate 2 (383 mg) and triphenylphosphine (253 mg) in dry tetrahydrofuran (10 ml) was stirred under nitrogen for 20 hours. To this was added triethylamine (5 ml) and water (13 ml) and the solution was heated at 40° for a further 24 hours. The reaction mixture was washed with ethyl acetate (20 ml), the organic phase re-extracted with water (5 ml) and the combined aqueous phases evaporated under vacuum. The residue was purified by preparative Hplc (Microsorb C18) using a water/acetonitrile/trifluoroacetic acid elution gradient. The freeze-dried solid obtained was taken up in methanol (2 drops) and precipitated using diethyl ether (10 ml) to give the title compound (215 mg) as a white powder.

m/z $MH^+$=432.3
Analysis Found: C, 45.8; H, 6.5; N. 7.75.
$C_{19}H_{33}N_3O_8 \cdot CF_3CO_2H$ requires C, 46.2; H, 6.3; N, 7.7

EXAMPLE 2

(4S,5R,6R)-5-Acetylamino6-(1R-heptylcarbamoyloxy-2R,3-dihydroxypropyl)-4-guanidino-5,6-dihydro4H-pyran-2-carboxylic acid trifluoroacetate Intermediate (3): (4S,5R,6R)-5-Acetylamino-6-(1R-heptylcarbamoyloxy-2R,3-dihydroxypropyl)-4-[2,3-bis(tert-butoxycarbonyl)-guanidino]-5,6-dihydro-4H-pyran-2-carboxylic acid methyl ester A solution of the compound of Example 1 (190 mg), triethylamine (0.1 ml) and N, N'-bis-t-butoxycarbonyl-1H-pyrazole-1-carboxamidine (179 mg) in dry methanol (3 ml) was stirred under nitrogen for 48 hours and then evaporated under vacuum. The residue obtained was purified by flash chromatography on a silica column (Merck 9385, ethyl acetate/glacial acetic acid 95:5) to give the title compound (218 mg) as a white solid.

NMR($d_6$-DMSO)δ8.17 (1H, d), 7.90 (1H, d), 7.13 (1H, t), 5.67 (1H, s), 4.80 (1H, d), 4.68 (1H, t), 4.39 (1H, d), 3.99 (1H, m), 3.83 (1H, m), 3.40 (1H), 3.24 (1H), 2.88 (2H, m), 1.92 (3H, s), 1.44 (9H, s), 1.40 (9H, s), 1.23 (10H, m), 0.86 (3H, t).
m/z $MH^+$=674.4

(4S,5R,6R)-5-Acetylamino6-(1R-heptylcarbamoyloxy-2R,3-dihydroxypropyl)-4-guanidino-5,6-dihydro4H-pyran-2-carboxylic acid trifluoroacetate A solution of Intermediate 3 (104 mg) in dry dichloromethane (1 ml) and trifluoroacetic acid (1 ml) was stirred under nitrogen for 2 hours and then evaporated under vacuum. The residue was taken up in methanol (2 drops) and precipitated using diethyl ether (5 ml) to yield a white solid which was purified by preparative Hplc (Microsorb C18) using a water/acetonitrile/trifluoroacetic acid elution gradient. The freeze-dried solid obtained was taken up in methanol (2 drops) and precipitated using diethyl ether (5 ml) to give the title compound (29 mg) as a white powder.

NMR($d_6$-DMSO)δ7.98 (1H, br d), 7.57 (1H, br d), 7.40 (3H, br s), 7.17 (1H, br t), 5.54 (1H, br d), 4.82 (1H, d), 4.2–4.38 (2H, 2xdd), 3.96 (1H, q), 3.82 (1H, td), ~3.3 (2H, m), 2.88 (2H, q), 1.77 (3H, s), 1.12–1.49 (10H, m), 0.87 (3H, t).
m/z $MH^+$=474. MS calcd. for $C_{20}H_{36}N_5O_8$ ($MH^+$): 474.2564. Found 474.2562
Analysis Found: C, 44.1; H, 6.6; N, 11.9.
$C_{20}H_{35}N_5O_8 \cdot CF_3CO_2H \cdot 0.5H_2O$ requires C, 44.3; H, 6.25; N, 11.7

EXAMPLE 3

(4S,5R,6R)-5-Acetylamino6-(1R-dodecylcarbamoyloxy-2R,3-dihydroxypropyl)-4-guanidino-5,6-dihydro-4H-pyran-2-carboxylic acid trifluoroacetate Intermediate (4): (4S,5R,6R)-5-Acetylamino-4-azido-6-[(S)-hydroxy-(2-oxo-[1,3]dioxolan-4R-yl)-methyl]-5,6-dihydro-4H-pyran-2-carboxylic acid benzhydryl ester A suspension of (4S,5R,6R)-5-Acetylamino-4-azido6-(1R,2R,3-trihydroxy-propyl)-5,6-dihydro-4H-pyran-2- carboxylic acid benzhydryl ester (10 g) was stirred in acetaldehyde diethyl acetal (250 ml) for one hour; this solution was stirred for a further 30 minutes after the addition of p-toluenesulphonic acid (30 mg) and then left to stand for 16 hours. The crystalline solid was filtered and dried to give the title compound (5 g) as a pale orange solid.
TLC silica (chloroform/methanol 9:1) Rf 0.30
m/z $MNH_4^+$=526

Intermediate (5): (4S,5R,6R)-5-Acetylamino-4-azido-6-[(S)-dodecylcarbamoyloxy-(2-oxo-[1,3]dioxolan-4R-yl)-methyl]-5,6-dihydro-4H-pyran-2-carboxylic acid benzhydryl ester To an ice-cold suspension of Intermediate 4 (2.96 g) in dry dichloromethane (115 ml) and dry acetonitrile (125 ml) was added 4-dimethylaminopyridine (877 mg) and n-dodecyl isocyanate (7.5 ml). The reaction mixture was heated at 45° under nitrogen for 89 hours. The reaction was quenched by the addition of methanol (6 ml), and concentrated to ~80 ml then added to 1M potassium dihydrogen orthophosphate solution (250 ml) and extracted with ethyl acetate (300 ml×2). The combined organic extracts were washed with concentrated aqueous NaCl (60 ml), dried ($Na_2SO_4$) and the solvent removed under vacuum to yield a yellow foam which was purified by flash chromatography on a silica column (Merck 9385, ethyl acetate/petroleum ether (40–60) 1:1) to give the title compound (1.247 g) as a yellow foam.
TLC silica (ethyl acetate/petroleum ether (40–60) 1:1) Rf 0.31
m/z $MH^+$=720.2, $MNa^+$=742.2

Intermediate (6): (4S,5R,6R)-5-Acetylamino-4-amino-6-[(S)-dodecylcarbamoyloxy-(2-oxo-[1,3]dioxolan-4R-yl)-methyl]-5 6-dihydro4H-pyran-2-carboxylic acid benzhydryl ester A mixture of Intermediate 5 (1.139 g) and triphenylphosphine (517 mg) in dry tetrahydrofuran (20 ml) was heated at 400 under nitrogen for 24 hours. To this was added triethylamine (11 ml) and water (17 ml) and the reaction mixture was heated at 40° for 2 hours and then evaporated to yield a yellow solid which was purified by flash chromatography on a silica column (Merck 9385, chloroform/methanol 15:1) to give the title compound (761 mg) as a yellow foam.
TLC silica (chloroform/methanol 15:1) Rf0.14
m/z MS calcd. for $C_{39}H_{56}N_3O_8$ ($MH^+$):694.4067. Found 694.4062

Intermediate (7): (4S,5R,6R)-5-Acetylamino-6-[(S-dodecylcarbamoyloxy-(2-oxo-[1,3]-dioxolan-4R-yl)-methyl]-4-[2,3-bis(tert-butoxycarbonyl)-guanidino-5,6-dihydro-4H-pyran-2-carboxylic acid benzhydryl ester A suspension of Intermediate 6 (670 mg) and bis (t-butoxycarbonyl)-1H-pyrazole-1-carboxamidine (390 mg) in dry tetrahydrofuran (8 ml) was stirred under nitrogen at 35° for 48 hours and then evaporated under vacuum to yield an off-white foam which was purified by flash chromatography on a silica column (Merck 9385, ethyl acetate/petroleum ether (40–60) 1:2) to give the title compound (815 mg) as a white solid.
TLC silica (ethyl acetate/petroleum ether (40–60) 1:2) Rf0.13
m/z $MH^+$=936.6

(4S,5R,6R)-5-Acetylamino -6-(1R-dodecylcarbamoyloxy-2R,3-dihydroxypropyl)-4-guanidino-5,6-dihydro4H-pyran-2-carboxylic acid trifluoroacetate A solution of Intermediate 7 (637 mg) in glacial acetic acid/water 4:1 (20 ml) was heated at 85° for 2 hours and then evaporated under vacuum to yield a white solid which was stirred in dry dichloromethane (6 ml) and trifluoroacetic acid (5 ml) for 26 hours. The solvent was removed under vacuum to yield a green foam which was purified by reverse phase silica column chromatography (Merck, LiChroprep RP-18, water/acetonitrile/trifluoroacetic acid 50:50:1) to give the title compound (209 mg) as a freeze-dried white powder.
NMR($d_6$-DMSO) δ7.98 (1H, br d), 7.57 (1H, br d), 7.36 (3H, br s), 7.18 (1H, br t), 5.57 (1H, br d), 4.83 (1H, dd), 4.33 (1H, dd), 4.25 (1H, dd), 3.97 (1H, q), 3.82 (1H, td), ~3.4 (2H, m), 2.88 (2H, q), 1.78 (3H, s), 1.1–1.47 (20H, m), 0.86 (3H, t).
m/z $MH^+$=544.3
Analysis Found: C,49.3; H,7.4; N, 10.8.
$C_{25}H_{45}N_5O_8 \cdot CF_3CO_2H$ requires C, 49.3; H, 7.05; N, 10.65

EXAMPLE 4

(4S,5R,6R)-5-Acetylamino-4-amino-6-{2R,3-dihydroxy-1R-[(6-tert-butoxycarbonylaminohexyl)-carbamoyloxy]-propyl}-5,6-dihydro-4H-pyran-2-carboxylic acid trifluoroacetate Intermediate (8): (4S,5R,6R)-5-Acetylamino-4-azido-6-[(S)-(4-nitro-phenoxycarbonyloxy)-(2-oxo-[1,3]-dioxolan-4R-yl)-methyl]-5,6-dihydro-4H-pyran-2-carboxylic acid methyl ester To a solution of (4S,5R,6R)-5-Acetylamino-4-azido-6-(1R,2R,3-trihydroxy-propyl)-5,6-dihydro-4H-pyran-2-carboxylic acid methyl ester (3.3 g) in dry pyridine (30 ml), under nitrogen, was added 4-nitrophenylchloroformate (2.42 g). After stirring at room temperature for 2.5 hours a further portion of 4-nitrophenylchloroformate (2 g) was added followed by 4-dimethylaminopyridine (3.05 g). Stirring was continued at room temperature for 3.5 hours. The solution was concentrated under vacuum and the residue was partitioned between 2M HCl (200 ml) and ethyl acetate (100 ml). The layers were separated and the aqueous phase was further extracted with ethyl acetate (100 ml ×2). The combined organic extracts were washed with saturated aqueous NaCl (60 ml), dried ($Na_2SO_4$) and the solvent removed under vacuum to yield a beige foam which was purified by flash chromatography on a silica column (Merck 9385, ethyl acetate/cyclohexane 2:1) to give the title compound (3.21 g) as a white foam.
NMR($d_6$-DMSO) δ8.36 (2H, d), 8.22 (1H, d), 7.61 (2H, d), 5.94 (1H, d), 5.50 (1H, t), 5.35 (1H, m), 4.72 (1H, t), 4.60 (1H, t), 4.40–4.50 (2H, m), 4.23 (1H, t), 3.78 (3H, s), 1.86 (3H, s).
TLC silica (ethyl acetate/cyclohexane 2:1) Rf0.16
m/z $MH^+$=522

Intermediate (9): (4S,5R,6R)-5-Acetylamino-4-azido-6-{(S)-[(2-oxo-[1,3]dioxolan-4R-yl)-(6-tert-butoxycarbonyl-aminohexyl)-carbamoyloxy]-methyl}-5,6-dihydro-4H-pyran-2-carboxylic acid methyl ester To a solution of Intermediate 8 (1.15 g) in dry pyridine was added 4-dimethylaminopyridine (648 mg) and N-Boc-1,6-diaminohexane hydrochloride (670 mg). The solution was stirred at room temperature for 18 hours. 2M aqueous hydrochloric acid (150 ml) was added to the solution and extracted with ethyl acetate (50 ml×2). The combined organic extracts were washed with saturated aqueous NaCl (10 ml), dried ($Na_2SO_4$) and the solvent removed under vacuum to yield a yellow foam which was purified by flash chromatography on a silica column (Merck 9385, ethyl acetate/ cyclohexane 4:1) to give the title compound (1.155 g) as a pale yellow foam.
NMR ($CDCl_3$) δ6.31 (1 H, br.d), 5.95 (3H, d), 5.42 (1H, dd), 4.5–5.2 (7H, m), 3.80 (3H, s), 3.0–3.4 (5H, m), 2.06 (3H, s), 1.50 (4H, m), 1.44 (9H, s), 1.34 (4H, m).
TLC silica (ethyl acetate/cyclohexane 4:1) Rf0.28
Analysis Found: C, 49.6; H, 6.4; N, 13.4
$C_{25}H_{38}N_6O_{11} \cdot 0.35 C_4H_8O_2$ requires C, 49.6; H, 6.45; N, 13.9

(4S,5R,6R)-5-Acetylamino-4-amino-6-{2R,3-dihydroxy-1R-[(6-tert-butoxycarbonylaminohexyl)-carbamoyloxy]-propyl}-5,6-dihydro-4H-pyran-2-carboxylic acid trifluoroacetate To a solution of Intermediate 9 (1.05 g) in dry tetrahydrofuran (40 ml) was added triphenylphosphine (610 mg) and the solution was stirred at room temperature for 18 hours. To this was added triethylamine (12 ml) and water (31 ml) and the solution was heated at 40° for a further 28 hours. The reaction mixture was evaporated to yield a yellow gum which was purified by flash reverse-phase chromatography (Merck 13900, water (containing trifluoroacetic acid 0.1 %)/acetonitrile 8:2). The gum obtained by freeze-drying was triturated vigorously for one hour at room temperature to give the title compound as a buff powder.
NMR($d_6$-DMSO) δ7.92 (1H, d), 7.13 (1H, t), 6.75 (1H, t), 5.70 (1H, s) 4.85 (1H, d), 4.34 (1H, d), 4.02 (1H, q), 3.85 (1H, t), 3.77 (1H, d), 3.25, 3.44 (2H, m), 2.90 (4H, m), 1.82 (3H, s), 1.18–1.42 (8H, m), 1.38 (9H, s).
m/z $MH^+$=533
Analysis Found: C, 47.65; H, 6.75; N, 8.8
$C_{23}H_{40}N_4O_{10}.CF_3CO_2H.0.25C_6H_{15}N$ requires C, 47.4; H, 6.7; N, 8.9

EXAMPLE 5

(4S,5R,6R)-5-Acetylamino-6-{1R-[(6-aminohexyl)carbamoyl-oxy]-2R,3-dihydroxy-propyl}-4-guanidino-5,6-dihydro-4H-pyran-2-carboxylic acid trifluoroacetate
Intermediate (10): (4S,5R,6R)-5-Acetylamino-6-{1R-[(6-tert-butoxy-carbonylaminohexyl)carbamoyloxy]-2,3-dihydroxypropyl}-4-[2,3-bis(tert-butoxycarbonyl)]guanidino-5,6-dihydro-4H-pyran-2-carboxylic acid A solution of the compound of Example 4 (0.75 g), triethylamine (0.5 ml) and N,N'-bis-(t-butoxycarbonyl)-1H-pyrazole-1-arboxamidine (0.54 g) in a mixture of dry tetrahydrofuran (10 ml) and dry methanol (3 ml) was stirred under nitrogen for 20 hours and then evaporated under vacuum. The residue was dissolved in ethyl acetate (100 ml), stirred vigorously with water (20 ml) and the pH of the mixture was adjusted to pH 2 with 2M hydrochloric acid. The organic layer was washed with saturated aqueous NaCl (20 ml), dried ($Na_2SO_4$), and the solvent removed under vacuum to yield a yellow foam which was purified by flash chromatography on a silica column (Merck 9385, chloroform/methanol 7:1) to give the title compound (0.37 g) as a white solid.
NMR ($d_6$-DMSO) δ11.42 (1H, s), 8.25 (1H, d), 7.95 (1H, d), 7.16 (1H, t), 6.75 (1H, t) 5.80 (1H, s), 4.82 (1H, d), 4.74 (1H, t), 4.43 (1H, d), 4.0 (4H, m), 3.25 (1H, m), 2.90 (4H, m) 1.76 (3H, s), 1.49 (9H, s), 1.38 (18H, s), 1.2–1.5 (8H, m).
TLC silica (chloroform/methanol 3:1) Rf0.21
m/z $MH^+$=775
(4S,5R,6R)-5-Acetylamino-6-{1R-[(6-aminohexyl)carbamoyloxy]-2R,3-dihydroxy-propyl}4-guanidino-5,6-dihydro-4H-pyran-2-carboxylic acid trifluoroacetate A solution of Intermediate 10 (325 mg) in trifluoroacetic acid (10 ml) was stirred under nitrogen for 1 hour and evaporated under vacuum. The residue was dissolved in water (10 ml), stirred for one hour and the water removed by lyophilisation to give the title compound (255 mg) as a white solid.
NMR ($d_6$-DMSO) δ7.97 (1H, d), 7.69 (2H, br.s), 7.6 (1H, d), 7.2 (3H, m), 5.72 (1H, s), 5.07 (1H, d), 4.85 (1H, d), 4.4 (2H, m), 4.33 (1H, t), 4.02 (1H, q), 3.83 (1H, m), 3.3 (1H, m), 3.4 (1H, m), 2.91 (2H, m), 2.78 (2H, m), 1.81 (3H, s), 1.2–1.6 (8H, m)
m/z $MH^+$=475
TLC silica (butanol/acetic acid/water 3:1:1) Rf0.17

EXAMPLE 6

(4S, 5R,6R)-5-Acetylamino-4-amino6-[1R-(1,1-dicyclohexylcarbamoyloxy)-2R,3-dihydroxypropyl]-5,6-dihydro-4H-pyran-2-carboxylic acid trifluoroacetate
Intermediate (11) (4S,5R,6R)-5-Acetylamino-4-azido-6-[(S)-(1,1-dicyclohexylcarbamoyloxy)-(2-oxo-[1,3]-dioxolan-4R-yl)-methyl]-5,6-dihydro-4H-pyran-2-carboxylic acid benzhydryl ester A mixture of Intermediate 4 (1 g) in dry pyridine, and dicyclohexylcarbamoyl chloride (1.46 g) was heated under nitrogen at 100° C. for six hours. The mixture was concentrated under vacuum and the residue treated with 30% citric acid. The aqueous mixture was extracted with ethyl acetate (50ml×2). The combined organic extracts were washed with 10% sodium hydrogen carbonate solution (20 ml), saturated aqueous NaCl (20 ml), dried ($Na_2SO_4$) and the solvent removed under vacuum to yield an orange foam which was purified by flash chromatography on a silica column (Merck 9385, chloroform: methanol 20:1) to give the title compound (0.69 g) as a colourless foam.
TLC silica (diethyl ether/pet.ether (40:60) 3:1) Rf0.14
Analysis Found: C, 65.6; H, 6.6; N, 9.4.
$C_{39}H_{49}N_5O_8$ requires C, 65.4; H. 6.9; N. 9.8
Intermediate (12) (4S,5R,6R)-5-Acetylamino-4-amino-6-[(S)-(1.1-dicyclohexylcarbamoyloxy)-(2-oxo-[1,3]dioxolan-4R-yl)-methyl]-5,6-dihydro-4H-pyran-2-carboxylic acid benzhydryl ester The title compound was prepared from Intermediate 11 analogously to the preparation of Intermediate 6 from Intermediate 5.
NMR ($CDCl_3$) δ7.3 (10H, m), 6.94 (1H, s), 6.1 (2H, m), 5.25 (1H, dd), 4.95 (1H, q), 4.6 (1H, dd), 4.4–4.1 (3H, m), 3.9 (1H, m), 3.6 (1H, m), 3.2 (2H, m), 2.05 (3H, s), 1.3 (3H, d), 1.8–1.0 (20H, m)
Analysis Found: C, 64.2; H, 6.9; N, 5.65
$C_{39}H_{51}N_3O_8.0.4CHCl_3$ requires C, 64.2; H, 7.0; N, 5.7
(4S, 5R,6R)-5-Acetylamino-4-amino-6-[1R-(1,1-dicyclohexylcarbamoyloxy)-2R,3-dihydroxypropyl]-5,6-dihydro-4H-pyran-2-carboxylic acid trifluoroacetate The title compound was prepared from Intermediate 12 analogously to the preparation of Example 3 from Intermediate 7.
MS calc. for $C_{24}H_{40}N_3O_8$ $MH^+$:498.281541
Found: 498.280751
Analysis Found: C, 45.0; H, 6.2; N, 5.6
$C_{24}H_{39}N_3O_8.2(CF_3CO_2H).H_2O$ requires: C, 45.2; H, 5.8; N, 5.65

EXAMPLE 7

(4S,5R,6R)-5-Acetylamino-6-[1R-(1 1-dicyclohexylcarbamoyloxy)-2R,3-dihydroxypropyl]-4-guanidino-5,6-dihydro-4H-pyran-2-carboxylic acid trifluoroacetate
Prepared analogously to Example 3.
Analysis Found: C, 45.5; H, 6.0; N, 9.5
$C_{25}H_{41}N_5O_8.2(CF_3CO_2H)$ requires: C, 45.4; H, 5.65; N, 9.1
TLC Rf=0.65, n-butanol: acetic acid: water, 3: 1:1

EXAMPLE 8

(4S,5R,6R)-5-Acetylamino-4-amino-6-[1R-benzylcarbamoyloxy-2R,3-dihydroxy-propyl]-5,6-dihydro-4H-pyran-2-carboxylic acid trifluoroacetate
Prepared analogously to Example 1.
MS calc. for $C_{19}H_{26}N_3O_8$ $MH^+$:424.171990
Found: 424.171552
TLC Rf=0.40, n-butanol: acetic acid: water, 3:1:1

EXAMPLE 9
(4S,5R,6R)-5-Acetylamino-4-amino-6-[1R-n-propylcarbamoyloxy-2R,3-dihydroxypropyl]-5,6-dihydro-4H-pyran-2-carboxylic acid trifluoroacetate
Prepared analogously to Example 1.
MS calc. for $C_{15}H_{26}N_3O_8$ MH+:376.171990
Found: 376.1732
TLC Rf=0.31, n-butanol: acetic acid: water, 3:1:1

EXAMPLE 10
(4S,5R,6R)-5-Acetylamino-4-amino-6-[1R-n-dodecylcarbamoyloxy-2R,3-dihydroxypropyl]-5,6-dihydro-4H-pyran-2-carboxylic acid trifluoroacetate
Prepared analogously to Example 1.
MS calc. for $C_{24}H_{44}N_3O_8$ MH$^+$:502.312841
Found: 502.314514
Analysis Found: C, 50.5; H, 7.35; N, 6.8
$C_{24}H_{43}N_3O_8.CF_3CO_2H$ requires: C, 50.7; H, 7.2; N, 6.8

EXAMPLE 11
(4S,5R,6R)-5-Acetylamino-4-amino-6-[1R-(1,1-diisopropylcarbamoyloxy)-2R,3-dihydroxypropyl]-5,6-dihydro4H-pyran-2-carboxylic acid trifluoroacetate
Prepared analogously to Example 6.
Analysis Found: C, 41.0; H, 5.5; N, 6.6
$C_{18}H_{31}N_3O_8.1.6\ CF_3CO_2H.H_2O$ requires: C, 41.2; H, 5.6; N, 6.8
TLC Rf=0.41, n-butanol: acetic acid: water, 3:1:1

EXAMPLE 12
(4S,5R,6R)-5-Acetylamino-6-[1R-(1,1-diisopropylcarbamoyloxy)-2R,3-dihydroxy-propyl]-4-guanidino-5,6-dihydro-4H-pyran-2-carboxylic acid trifluoroacetate
Prepared analogously to Example 3.
MS calc. for $C_{19}H_{34}N_5O_8$ MH$^+$:460.240739
Found: 460.241167
Analysis Found: C, 42.8; H, 6.4; N, 11.45
$C_{19}H_{33}N_5O_8.CF_3CO_2H.H_2O$ requires: C, 42.6; H, 6.1; N, 11.8

EXAMPLE 13
(4S,5R,6R)-5-Acetylamino-4-amino-6-[1R-(1,1-dibenzylcarbamoyloxy)-2R,3-dihydroxypropyl]-5,6-dihydro-4H-pyran-2-carboxylic acid trifluoroacetate
Prepared analogously to Example 4.
MS calc. for $C_{25}H_{32}N_3O_8$ MH+:514.218940
Found: 514.218791
TLC Rf=0.51, n-butanol: acetic acid: water, 3:1:1

EXAMPLE 14
(4S,5R,6R)-5-Acetylamino-4-amino-6-[1R-(1,1di-n-propylcarbamoyloxy)-2R,3-dihydroxypropyl]-5,6-dihydro-4H-pyran-2-carboxylic acid trifluoroacetate
Prepared analogously to Example 4.
MS calc. for $C_{18}H_{32}N_3O_8$ MH$^+$:418.218940
Found: 418.219123
Analysis Found: C, 41.7; H. 5.7; N. 6.8
$C_{18}H_{31}N_3O_8.1.5\ CF_3CO_2H.H_2O$ requires: C, 41.6; H, 5.7; N. 6.9

EXAMPLE 15
(4S,5R,6R)-5-Acetylamino-4-amino-6-[1R-cyclohexylcarbamoyloxy-2R,3-dihydroxypropyl]-5,6-dihydro-4H-pyran-2-carboxylic acid trifluoroacetate
Prepared analogously to Example 6.
Analysis Found: C, 42.6; H, 5.7; N, 7.2
$C_{24}H_{29}N_3O_8.CF_3CO_2H.2H_2O$ requires: C, 42.5; H. 6.1; N, 7.4
TLC Rf=0.44 n-butanol: acetic acid: water, 3:1:1

EXAMPLE 16
(4S,5R,6R)-5-Acetylamino-6-[1R-(1,1-dihexylcarbamoyloxy)-2R,3-dihydroxy-propyl]-4-guanidino-5,6-dihydro-4H-pyran-2-carboxylic acid trifluoroacetate
Prepared analogously to Example 5.
Analysis Found: C, 46.3; H. 6.8; N. 9.6
$C_{25}H_{45}N_5O_8.1.3\ CF_3CO_2H.1.3H_2O$ requires: C, 46.3; H, 6.9; N, 9.8
TLC Rf=0.59, n-butanol : acetic acid: water, 3:1:1

EXAMPLE 17
(4S,5R,6R)-5-Acetylamino-4-amino-6-[1R-(1,1-n-heptylbenzylcarbamoyloxy)-2R,3-dihydroxypropyl]-5,6-dihydro-4H-pyran-2-carboxylic acid trifluoroacetate
Prepared analogously to Example 4.
Analysis Found: C, 48.7; H, 6.0; N, 5.85
$C_{26}H_{39}N_3O_8.1.5\ CF_3CO_2H.1.5H_2O$ requires: C, 48.4; H, 6.1; N, 5.8
TLC Rf=0.53, n-butanol: acetic acid: water, 3:1:1

EXAMPLE 18
(4S5R,6R)-5-Acetylamino-6-[1R-(1,1-n-heptylbenzylcarbamoyloxy)-2R,3-dihydroxypropyl]-4-guanidino-5,6-dihydro-4H-pyran-2-carboxylic acid trifluoroacetate
Prepared analogously to Example 5.
Analysis Found: C, 48.3; H. 5.8; N, 9.6
$C_{27}H_{41}N_5O_8.1.5\ CF_3CO_2H.0.5H_2O$ requires: C, 48.45; H, 5.9; N, 9.4
TLC Rf=0.58, n-butanol : acetic acid: water, 3:1:1

EXAMPLE 19
(4S,5R,6R)-5-Acetylamino-4-amino-6-[1R-[(6-aminohexyl)carbamoyloxy]-2R,3-dihydroxypropyl]-5,6-dihydro-4H-pyran-2-carboxylic acid trifluoroacetate
Prepared analogously to Example 5.
MS calc. for $C_{18}H_{33}N_4O_8$ MH$^+$:433.229839
Found: 433.231597
TLC Rf=0.12, n-butanol: acetic acid: water, 3:1:1

EXAMPLE 20
Inhibition of Influenza Virus

The ability of compounds of the invention to inhibit the mutiplication of influenza virus was determined using the method described in WO91/16320. The compounds of the Examples showed activity against influenza A and influenza B virus in this plaque reduction assay. For example, compounds of Examples 1 to 5 had $I_{50}$ values for influenza A and influenza B of less than 7 μg/ml.

Pharmaceutical formulations
Intranasal Formulations

|  | % w/w |
|---|---|
| (i) AQUEOUS SOLUTION | |
| Compound of formula (I) | 10.00 |
| Benzalkonium chloride | 0.04 |
| Phenylethyl alcohol | 0.40 |
| Purified water | to 100% w/w |
| (ii) AQUEOUS COSOLVENT SOLUTION | |
| Compound of formula (I) | 10.00 |
| Benzalkonium chloride | 0.04 |

-continued

|  | % w/w |
| --- | --- |
| Polyethylene glycol 400 | 10.0 |
| Propylene glycol | 30.0 |
| Purified water | to 100% w/w |
| (iii) AEROSOL FORMULATION | |
| Compound of formula (I) | 7.5 |
| Lecithin | 0.4 |
| Propellant 11 | 25.6 |
| Propellant 12 | 66.5 |
| (iv) DRY POWDER FORMULATION | |
| Compound of formula (I) | 40.0 |
| Lactose | 60.0 |

These formulations are prepared by admixture of the active ingredient and excipients by conventional pharmaceutical methods.

We claim:

1. A compound of formula (I):

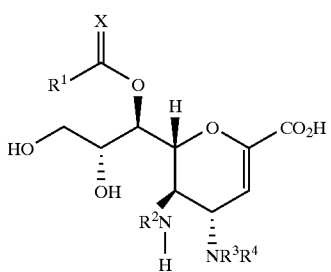

(I)

wherein $R^1$ represents $NR^5R^6$, wherein $R^5$ represents H or a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group; and $R^6$ represents a hydrocarbon group optionally substituted by one or more of Br, Cl, F, I, $CF_3$, $NR^7R^8$, $CO_2R^9$, $CONR^7R^8$, $COR^9$, $OR^{10}$ or $SR^{10}$, or a heteroaromatic group;

$R^2$ represents a group $SO_2R^9$ or $COR^9$;

$R^3$ represents H, $C_{1-6}$ alkyl or $C(=NR^{11})NR^{12}R^{13}$;

$R^4$ represents H or $C_{1-6}$ alkyl;

$R^7$ and $R^8$ each independently represent H, $C_{1-6}$ alkyl or $COR^9$;

$R^9$ represents $C_{1-6}$ alkyl optionally substituted by one or more halogen atoms;

$R^{10}$ represents H, $C_{1-6}$ alkyl or phenyl;

$R^{11}$, $R^{12}$ and $R^{13}$ each independently represent H, $C_{1-6}$-alkyl, amino, hydroxy, cyano or nitro; and X represents O or S;

or a pharmaceutically acceptable derivative thereof.

2. A compound as claimed in claim 1 wherein $R^5$ represents H, $C_{1-5}$ alkyl or benzyl.

3. A compound as claimed in claim 1 wherein $R^6$ represents optionally substituted $C_{1-20}$ alkyl or benzyl.

4. A compound as claimed in claim 1 wherein $R^2$ represents $COR^9$.

5. A compound as claimed in claim 1 wherein $NR^3R^4$ represents amino or guanidino.

6. A compound as claimed claim 1 wherein X represents O.

7. A compound of formula (Ia):

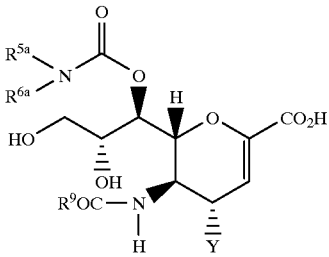

(Ia)

wherein:

$R^9$ is as defined for formula (I);

$R^{5a}$ represents H, $C_{1-12}$ alkyl or benzyl;

$R^{6a}$ represents optionally substituted $C_{1-12}$ alkyl or benzyl;

Y represents an amino or guanidino group;

or a pharmaceutically acceptable salt or ester thereof.

8. A compound selected from the group consisting of:

(4S,5R,6R)-5-Acetylamino-6-(1R-heptylcarbamoyloxy-2R,3-dihydroxy-propyl)4-guanidino-5,6dihydro-4H-pyran-2-carboxylic acid;

(4S,5R,6R)-5-Acetylamino6-(1R-dodecylcarbamoyloxy-2R,3-dihydroxy-propyl)-4-guanidino-5, 6-dihydro-4H-pyran-2-carboxylic acid;

(4S,5R,6R)-5-Acetylamino-6-{1R-[(6-amino-hexyl)carbamoyloxy]-2R,3-dihydroxypropyl}-4-guanidino-5,6-dihydro-4H-pyran-2-carboxylic acid;

and pharmaceutically acceptable derivatives thereof.

9. A method of treating viral infection in a mammal including man comprising administration of a effective amount of a compound as claim in claim 1.

10. A method as claimed in claim 9 for treatment of an influenza virus infection.

11. A pharmaceutical formulation comprising a compound as claimed in claim 1 together with a pharmaceutically acceptable carrier.

12. A pharmaceutical formulation as claimed in claim 11 suitable for administration to the respiratory tract.

13. A process for the preparation of a compound of formula (I) as defined in claim 1, which process comprises:

(A) reduction of the azide group of a compound of formula (II):

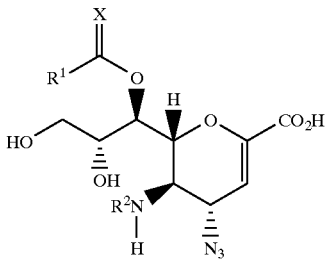

(II)

or a protected derivative thereof, wherein $R^1$ and $R^2$ are as defined for compounds of formula (I); or (B) reaction of intermediates of formula (III):

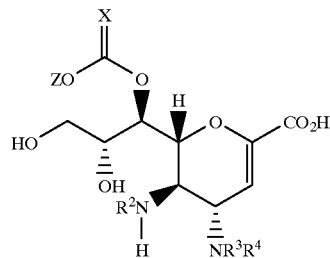

(III)

or a protected derivative thereof, wherein $R^2$, $R^3$ and $R^4$ are as defined in formula (I) and Z represents an activating group, with a compound of formula $HNR^5R^6$.

14. A compound of formula (II):

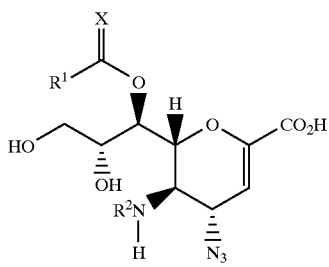

(II)

wherein $R^1$ and $R^2$ are as defined in formula (I).

15. A compound of formula (III):

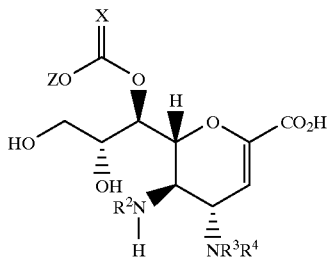

(III)

wherein $R^2$, $R^3$ and $R^4$ are as defined in formula (I) and Z represents an activating group.

16. A compound of formula (IV):

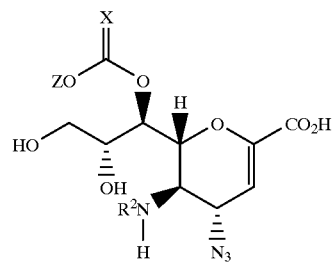

(IV)

wherein $R^2$ is as defined in formula (I) and Z represents an activating group.

* * * * *